US012721518B2

(12) United States Patent
Zheleznyak et al.

(10) Patent No.: US 12,721,518 B2
(45) Date of Patent: Sep. 1, 2026

(54) EYE SCOPES

(71) Applicant: Clerio Vision, Inc., Rochester, NY (US)

(72) Inventors: Leonard Zheleznyak, Pittsford, NY (US); John Weberg, Reno, NV (US)

( * ) Notice: Subject to any disclaimer, the term of this patent is extended or adjusted under 35 U.S.C. 154(b) by 558 days.

(21) Appl. No.: 18/355,567

(22) Filed: Jul. 20, 2023

(65) Prior Publication Data

US 2024/0032789 A1 Feb. 1, 2024

Related U.S. Application Data

(60) Provisional application No. 63/392,684, filed on Jul. 27, 2022.

(51) Int. Cl.
*A61B 3/117* (2006.01)

(52) U.S. Cl.
CPC .................................... *A61B 3/117* (2013.01)

(58) Field of Classification Search
CPC ..... A61B 3/117; A61B 1/00002; A61B 1/005; A61B 3/0008; A61B 3/0016; A61B 3/0075; A61B 3/022; A61B 3/024; A61B 3/102; A61B 3/1005; A61B 2576/00; A61B 5/0004; A61B 3/1015; A61B 3/1025; A61B 3/103; A61B 3/1035; A61B 3/11; A61B 3/113; A61B 3/107; A61B 3/111; A61B 3/112
See application file for complete search history.

(56) References Cited

U.S. PATENT DOCUMENTS 10,932,901 B2 3/2021 Zheleznyak
2012/0257167 A1 10/2012 Gille
2018/0173009 A1 6/2018 Knox
2020/0214561 A1* 7/2020 Kalina, Jr. ........... A61B 3/0091
2020/0367745 A1 11/2020 Kalina

OTHER PUBLICATIONS

Phase resolved OCT to measure laser induced refractive index change (LIRIC) in hydrogel, Investigative Ophthalmology & Visual Science Jun. 2021, vol. 62, 1813 (https://iovs.arvojournals.org/article.aspx?articleid=2775053).
LIRIC: A Novel LVC Treatment, Review of Ophthalmology, Feb. 10, 2022 (https://www.reviewofophthalmology.com/article/liric-a-novel-lvc-treatment ).

* cited by examiner

*Primary Examiner* — Brandi N Thomas
(74) *Attorney, Agent, or Firm* — Scott Catlin; Guy Cumberbatch

(57) ABSTRACT

Scopes for viewing interior chambers of the eye include a refractive hydrogel polymer button formed by femtosecond laser micro-machining. The refractive button is sandwiched between two transparent plates and mounted on an ocular adapted to be placed directly on the cornea. A physician may look directly through the scope to see anatomical structures at very steep angles within the eye, such as to function as a gonioscope when viewing the anterior chamber angle. The scopes can be modified for viewing a variety of anatomical structures within the eye, and can also be used in conjunction with treatments such as by guiding injections or laser procedures. The refractive button has at least one region with a wavefront pattern of linear steps formed therein. Multiple regions with different wavefront patterns provide the physician with greater flexibility. The refractive button may be rotated relative to the ocular to further customize the image.

30 Claims, 8 Drawing Sheets

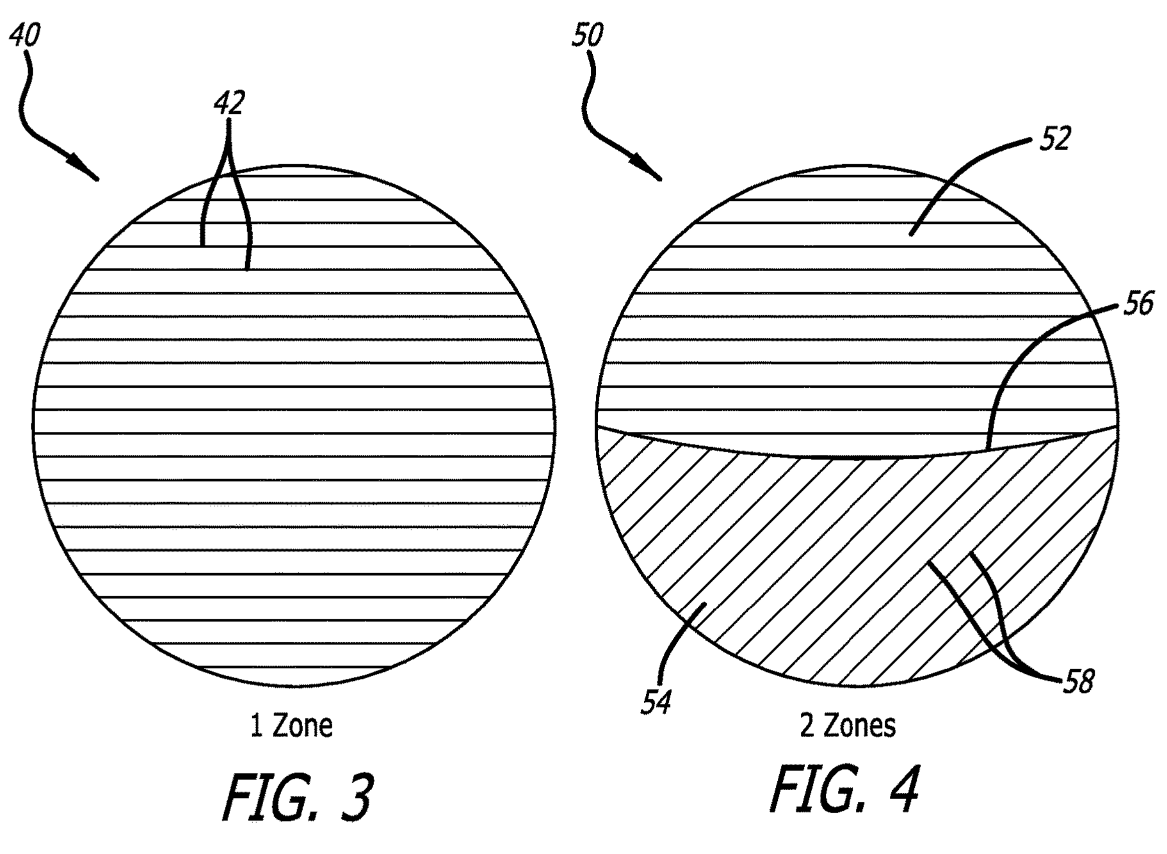
FIG. 3
FIG. 4
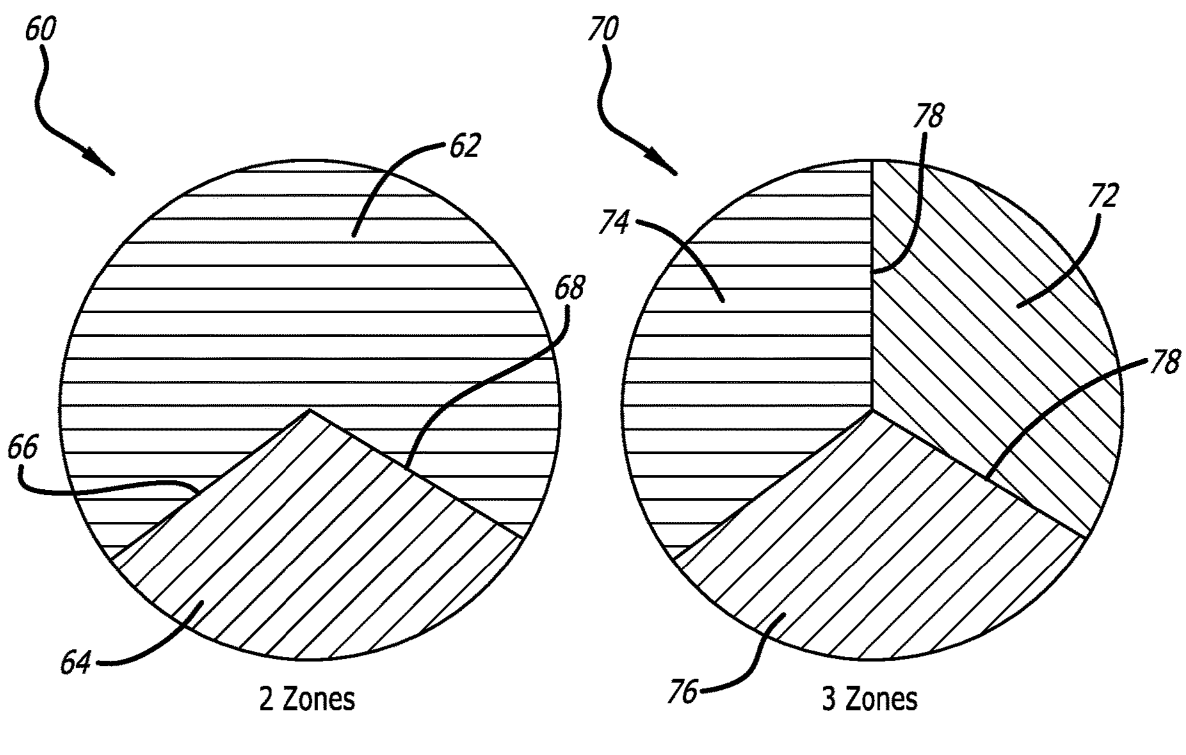
FIG. 5
FIG. 6

Z
120
140
142
132
130
134
136
122
124
Cornea
Anterior chamber
Anterior chamber angle

EYE SCOPES

RELATED APPLICATIONS

The present application claims priority under 35 U.S.C. § 119 to U.S. Provisional Application Ser. No. 63/392,684, filed Jul. 27, 2022.

FIELD OF THE INVENTION

The present application is directed to scopes for viewing interior chambers of the eye and, in particular, to improved scopes for viewing structures along refractive angles.

BACKGROUND OF THE INVENTION

Glaucoma is a blinding optic neuropathy affecting approximately 70 million individuals worldwide. Its main risk factor is elevated intraocular pressure (IOP). The trabecular meshwork, a group of tiny canals located in the iridocorneal or anterior chamber angle, constitutes the main pathway for drainage of aqueous humor out of the eye. The trabecular meshwork controls the IOP by regulating outflow of aqueous humor from the anterior chamber of the eye into the adjacent Schlemm' s canal and then via aqueous vein collector channels into the venous system. Dysfunction of the trabecular meshwork is one major cause of IOP elevation.

The classification of glaucoma relies heavily upon knowledge of the anterior chamber anatomy, particularly that of the anterior chamber angle. The anterior chamber of a human eye is commonly evaluated with an illuminated microscope (e.g., a slit lamp stereomicroscope), hut the anterior chamber angle is typically difficult to see or hidden from ordinary view because of the oblique angle of view that is required to see these anatomical structures, as well as the total internal reflection of light rays emanating from the anterior chamber angle structures. Gonioscopy is a technique used for viewing the inner parts of the eye, such as the anterior chamber of the eye (e.g., the anterior chamber angle) and its anatomical elements (e.g., trabecular meshwork, Schlemm's canal, scleral spur, iris root, etc.) prior to or during a surgical procedure, for evaluation, and/or for classification of normal and abnormal structures. Besides glaucoma, there are many other ophthalmological diseases and disorders, such as retinal diseases and disorders, for example, macular degeneration, diabetic retinopathy, various genetic disorders and cancers in the eye, retinal detachment, and injuries throughout the eye.

Devices used for gonioscopy are known as gonioscopes or goniolenses. During surgical applications, it may be hand held by the surgeon in place over the patient's cornea while he/she is performing the surgical procedure. There are two main types of conventional goniolenses—direct and indirect. Direct goniolenses are transparent devices placed directly on the cornea which bend light from the anterior chamber angle through an outer hemispherical surface. Direct goniolenses require the patient to be lying down, and so they cannot be so easily used with an ordinary slit lamp in an optometric environment. These goniolenses are often bulky and provide distorted views. Indirect goniolenses use mirrors to reflect a reverse image from the iridocorneal angle into the direction of the observer. A Zeiss indirect goniolens employs prisms in the place of mirrors to correct the reverse image, though the instrument is bulky and expensive. Moreover, an indirect goniolens reverses the image making it backwards or opposite from the real image, thereby making it hard for a doctor or surgeon to maintain anatomical correctness or to operate where their movements in the eye appear opposite to the movements they are making.

Although various gonioscopes exist, there are a number of drawbacks and there remains a need for improved gonioscopic devices, as well as better scopes in general for diagnoses and treatments, especially for regions of the eye outside of the central visual axis or fovea, and for views and treatments at higher angles in the eye in the periphery.

SUMMARY OF THE INVENTION

This application presents scopes for directly viewing interior chambers of the eye and, in particular, improved scopes for viewing structures at steep angles within the eye. The scopes may be configured and utilized as gonioscopes for viewing the anterior chamber angle. Other diagnostic applications include using the scope to diagnose disease within various regions of the eye. Peripheral retinal imaging is another application, as is imaging haptics on an intraocular lens (IOL), ciliary structures, or the peripheral crystalline lens and capsular bag, which are normally hidden from direct view behind the iris.

The scopes described herein may also be used in conjunction with various treatments. For example, the scopes may be used to guide injections or laser radiation for correcting retinal detachment or operating on blood vessels. The scopes may enable an ophthalmologist to treat peripheral regions of the retina which have previously been outside of the field of view. The scopes may also be used to treat posterior capsule opacification, gene therapy, or for implanting an Argus retinal prosthetic. U.S. Pat. Nos. 5,476,445 and 6,050,970 to Dr. George Baerveldt, et al. disclose implants or shunts often used in long-term glaucoma treatment, and the scope described herein may be used in conjunction with the installation of such shunts.

A first embodiment of an eye scope comprises a polymer member having a refractive index and a proximal and distal side, with the distal side towards an eye. The polymer member has a central axis perpendicular to both the proximal and distal sides and an internal layer modified by femtosecond laser micromachining to alter the refractive index to have a wavefront pattern that deflects light passing through the polymer member from the distal to the proximal side. A transparent rigid support member is positioned on a side of the polymer member, wherein an observer may look through the scope to view interior details of an eye that are at an angle from the central axis of the eye.

The first embodiment of the eye scope may further comprise a transparent patient contact interface positioned distal to the rigid support member which is positioned distal to the polymer member, wherein the scope may be placed with the patient contact interface in contact with a patient's cornea. A second polymer member may be positioned on the distal side of the rigid support member. The second polymer member also has an internal layer modified by femtosecond laser micromachining to have a wavefront pattern that deflects light passing through the second polymer member from the distal to the proximal side. One or both of the first and second polymer members is/are rotatable relative to the patient contact interface.

A second eye embodiment of an eye scope comprises a polymer member having a refractive index and a proximal and distal side, with the distal side towards an eye, and wherein the polymer member has a central axis perpendicular to both the proximal and distal sides. The polymer member has an internal layer modified by femtosecond laser micromachining to alter the refractive index to have a wavefront pattern that deflects light passing through the polymer member from the distal to the proximal side. A transparent first rigid support member is positioned on a distal side of the polymer member and a transparent second rigid support member is positioned on the proximal side of the polymer member, the first and second rigid support members and the polymer member being affixed together in a subassembly. A transparent patient contact interface is positioned distal to the subassembly, wherein the scope may be placed with the patient contact interface in contact with a patient's cornea, and the subassembly is rotatable relative to the patient contact interface. An observer may look through the scope to view interior details of an eye that are at an angle from the central axis of the eye.

The second eye scope may further include a second polymer member having an internal layer modified by femtosecond laser micromachining to have a wavefront pattern that deflects light passing through the second polymer member from the distal to the proximal side, the second polymer member being positioned between the first rigid support member and the patient contact interface.

In either embodiment of the eye scope, the polymer member(s) may be flat on both sides. The polymer member(s) may be a hydrogel polymer. In addition, the eye scopes may further include a masking element positioned on the proximal side of the second rigid support member. The masking element may be rotatable relative to the second rigid support member. The masking element may be opaque except for an open or clear window in one segment thereof.

In either embodiment of the eye scope, the polymer member internal layer has two or more regions, wherein each region has a different optical effect caused by the femtosecond micromachining to alter refractive index in each region. The different optical effect on the light passing through the polymer member in each region is desirably at least one of the following: deflection angle; optical power or magnification; defocus; cylinder; wavefront aberrations; multifocality; chromatic aberrations; and masking elements. The eye scopes may be configured to image an anterior chamber angle of the eye through the light deflected through the polymer member. Further, the scopes may be configured to image annular regions of the retina at 0-15 degrees and 15-30 degrees through the light deflected through the polymer member.

BRIEF DESCRIPTION OF THE DRAWINGS

Features and advantages of the present invention will become appreciated as the same become better understood with reference to the specification, claims, and appended drawings wherein:

FIG. 3 is a top plan view of an exemplary refractive member or button used in the scopes of the present application;

FIG. 4 is a top plan view of an alternative refractive member or button having two different refractive regions thereon;

FIG. 5 is a top plan view of an alternative refractive member or button having two different refractive regions thereon;

FIG. 6 is a top plan view of an alternative refractive member or button having three different refractive regions thereon;

DETAILED DESCRIPTION OF THE PREFERRED EMBODIMENTS

The present application provides new viewing scopes for the eye which, at a minimum, greatly simplify existing gonioscopes. Current gonioscopes are relatively bulky and expensive, and utilize minors which transpose the viewing field into a reverse image. An ophthalmologist looking through a gonioscope sees things in reverse, which greatly complicates not only diagnosis but the manipulation of any instruments used in treatment. Double-minor systems do not exist in clinical practice. The present application discloses scopes which permit direct viewing of the interior chamber of the eye which is significantly more intuitive for the doctor.

Figure 1:
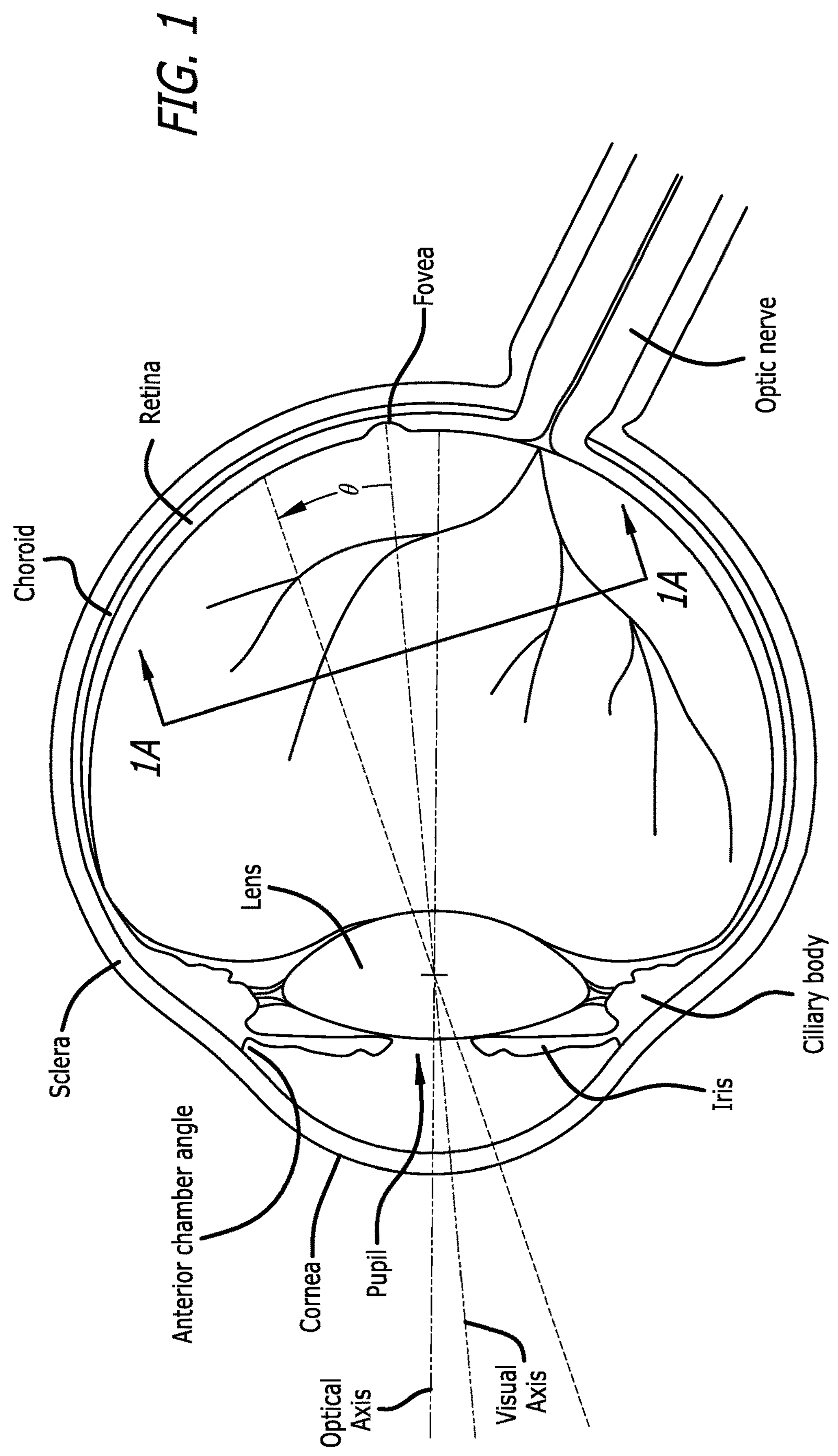
FIG. 1 shows an anatomical cross-section of the eye illustrating major internal structures.

FIG. 1 shows an anatomical diagram of the human eye illustrating major internal structures. The aqueous humour is a transparent water-like fluid similar to plasma secreted from the ciliary body or processes, a structure supporting the lens. Aqueous humour production must be balanced by an equal rate of aqueous humour drainage. Small variations in the production or outflow of aqueous humour will have a large influence on the intraocular pressure. The drainage route for aqueous humour flow is first through the posterior chamber, then the narrow space between the posterior iris and the anterior lens, from there through the pupil to the anterior chamber. The aqueous humour exits the eye through the trabecular meshwork at the anterior chamber angle and into circular Schlemm's canal (a channel at the limbus, i.e., the joining point of the cornea and sclera). In glaucoma, flow is reduced through the trabecular meshwork due to the degeneration and obstruction thereof. Loss of aqueous humor absorption leads to increased resistance and thus a chronic, often painless buildup of pressure in the eye. Increased pressure leads to various symptoms, including blindness. Diagnosing early-stage glaucoma requires examining the trabecular meshwork at the anterior chamber angle.

Figure 1A:
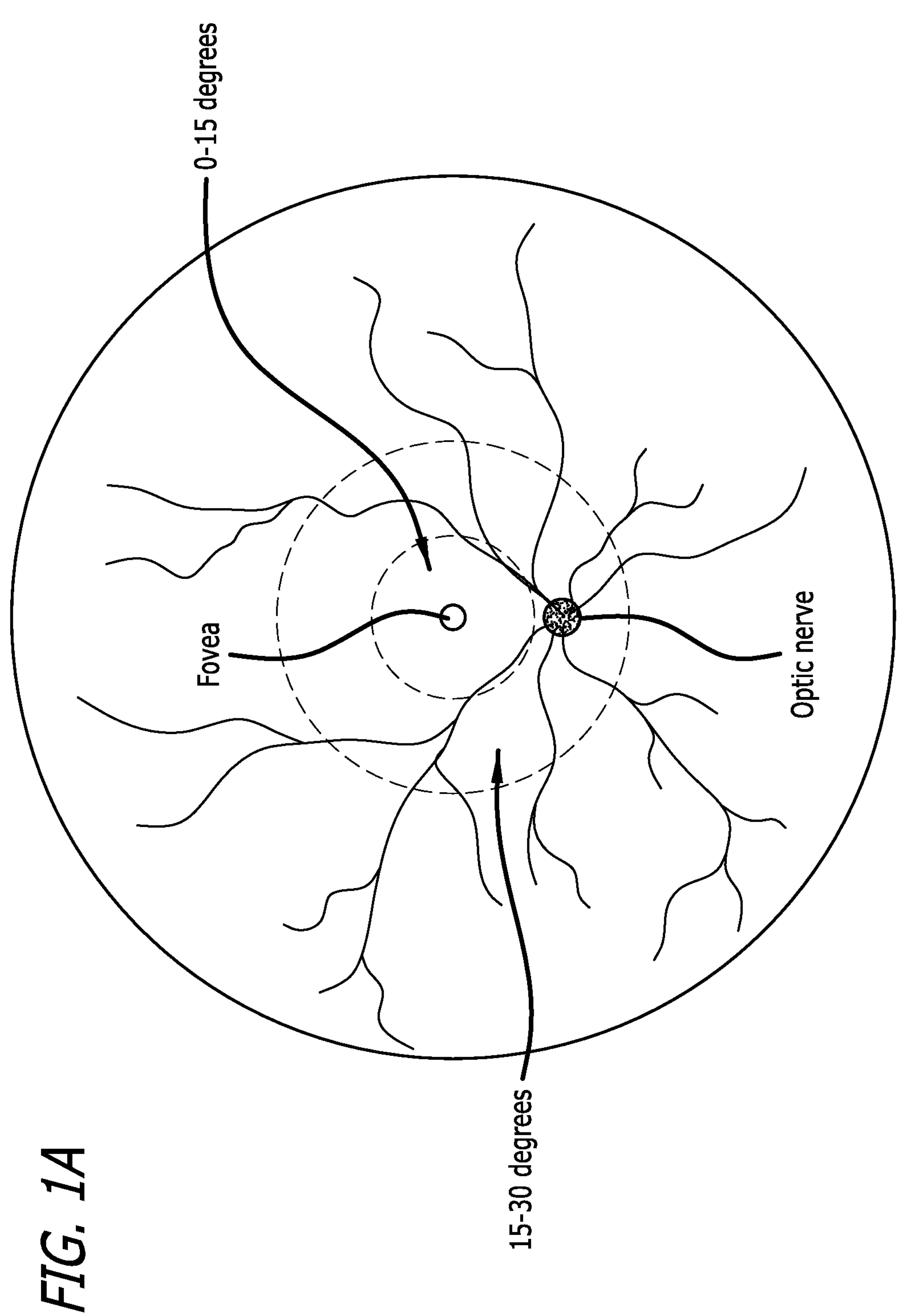
FIG. 1A is an interior view of the retina as seen from line 1A-1A in FIG. 1.

FIG. 1A is an interior view of the retina as seen from line 1A-1A in FIG. 1, that centers on the Fovea. FIG. 1 indicated the central visual axis which extends through the lens to the Fovea, as well as the optical axis which passes straight through the lens along its central axis. FIG. 1A shows two regions around the periphery of the Fovea in ranges of degrees from the central visual axis—i.e., annular regions of the retina at 0-15 degrees and 15-30 degrees. These regions may be targeted with the eye scope of the present application using different sections of refractive layers in the scope, as will be explained.

Figure 2:
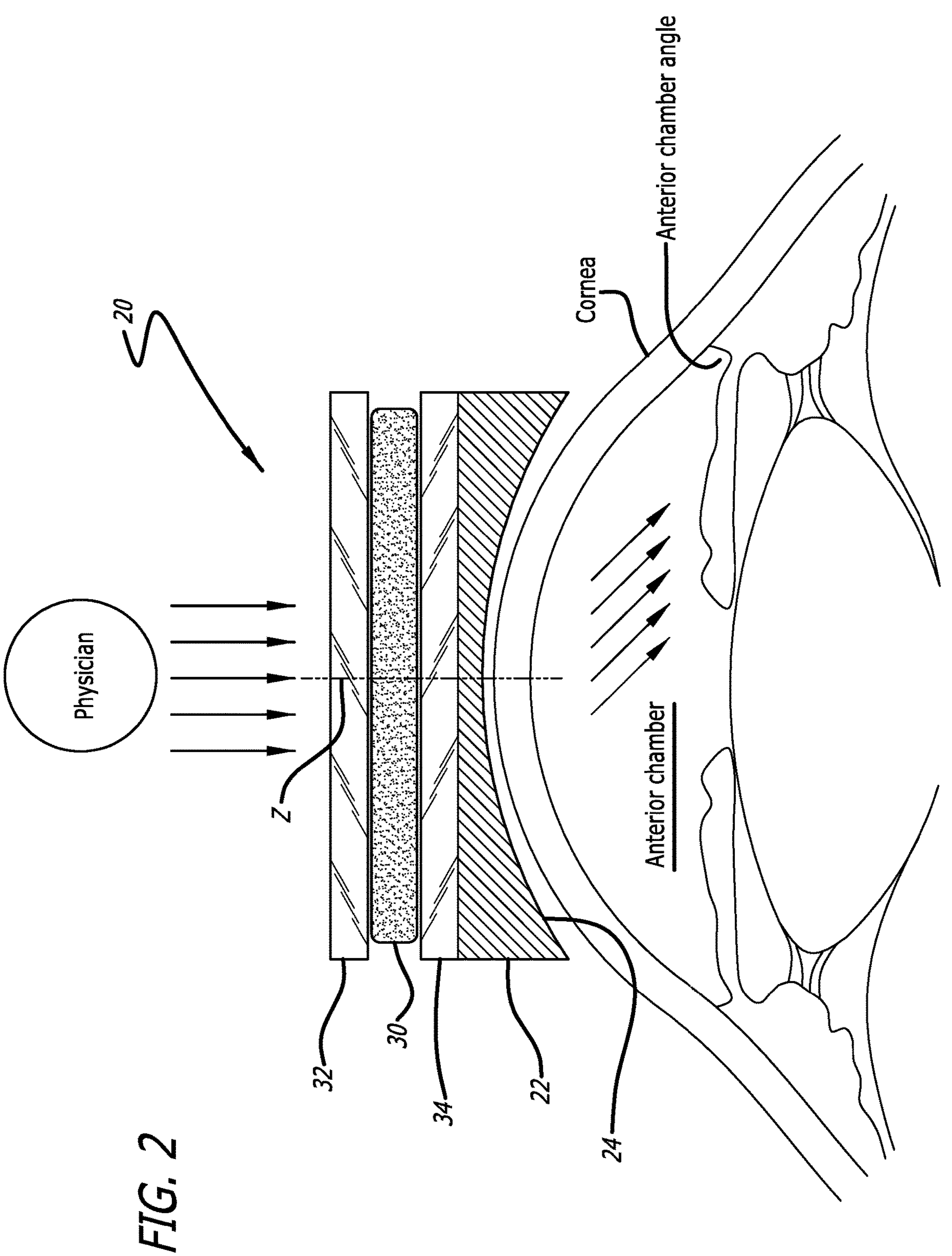
FIG. 2 is a schematic axial sectional view of an exemplary scope of the present application used for imaging an anterior chamber angle.

FIG. 2 is a schematic view of an exemplary scope 20 of the present application used for imaging tissue at the anterior chamber angle. A physician looks directly into the scope 20 which refracts and/or diffracts light from various angles straight back parallel to the central axis Z of the scope and the eye's visual axis. In the illustration, the physician looks at the anterior chamber angle directly through the middle of the scope 20.

The scope 20 comprises a patient contact interface sometimes called an ocular 22 having a curved distal surface 24 for contacting the cornea, often with the use of an index matching lubricating fluid or gel. The refractive component of the scope 20 is provided by a slim circular refractive layer in the form of a disk- or button-shaped refractive member 30 flanked by one slim plate or sandwiched between two support members or slim plates 32, 34. The term "plates" is used here for transparent rigid support members that flank the polymer refractive member 30 when in the form of a flat disk or button. However, the refractive member 30 may be in the form of a cylinder or other more three-dimensional structure (i.e., not a slim disk or button), with the consequence that the rigid support members are shaped less like plates and more like cups, or in some other form. Therefore, the term "support members" encompasses a number of such different shapes, including the slim plates 32, 34. Each of the plates 32, 34 as well as the ocular 22 are desirably transparent plastic or glass members with neutral refractive indices so as not to bend or otherwise affect light transmission therethrough. Outer housing members are not shown but are typically included to protect the aforementioned scope 20 components from dirt or damage. Such outer housing members may be made of various plastics, glasses or metals. The housing could also include a suction cup to hold the scope on the eye.

A preferred method of forming a refractive section or layer within the disk- or button-shaped refractive member 30 is to "write" a wavefront pattern directly into the contact lens by use of femtosecond laser micromachining. Techniques for such laser machining within structures is known from their use in LASIK surgery, as well as for contact lens modification for vision correction. For instance, work at the University of Rochester, NY as described in LIRIC: a Novel LVC Treatment, in the Review of Ophthalmology, Feb. 10, 2022, as well as U.S. Pat. No. 10,932,901 to Zheleznyak and U.S. Publication No. 2018/0173009 to Knox describe various such uses of femtosecond laser micromachining. The term "LIRIC" as used herein refers to laser-induced refractive index change of an optical structure. A LIRIC-modified optical structure has an internal section or layer (i.e., LIRIC layer) modified by femtosecond laser micromachining to have a wavefront pattern that deflects light passing through the optical structure.

In one embodiment, the distal plate 34 is coupled to the ocular 22 so as to be relatively rotatable, while the distal plate 34, refractive member 30 and proximal plate 32 are affixed together. In this arrangement, the upper three components may be rotated about the ocular 22 to change the angle of viewing into the eye. In some embodiments the various components may be rotated separately or relative to each other. There may in some embodiments be two refractive components that are rotatable relative to each other—for example, to alter direction of view and magnification (See FIG. 11). One of the members could include a LIRIC-modified optical structure to add power for magnification, or alternatively two translatable plates may be used in an Alverez lens configuration to variably change defocus. An "Alvarez lens" is described in Barbero, Sergio. "The Alvarez and Lohmann refractive lenses revisited." *Optics express* 17.11 (2009): 9376-9390. Expressly incorporated herein by reference.

It is also conceivable that the distal support member 34 could be curved on one or both sides to accommodate corneal curvature, like for comfort or less eye pressure, and to assume the function of the ocular 22, which is then omitted. The refractive member 30 could conform to that curvature on either side too. If the refractive member 30 is so curved, the wavefront induced therein would account for the curvature in terms of the viewing aspects and optical quality seeing into the eye.

The refractive member 30 may be made from a number of materials, though a hydrogel polymer is preferred, or another material, such as silicone, acrylic, silicone hydrogel (SiHy), and the like.

The refractive properties of the disk- or button-shaped refractive member 30 are established by laser micro-machining or "writing" a plurality of angled steps in a layer within the button. In one embodiment, the refractive member 30 has an axial thickness of between 10 μm and 10 mm, and the diffractive LIRIC layer within the bottom has a thickness of around 20-30 μm, a small percentage of the overall thickness (e.g., 10% of the total thickness for the case of a 250 um button axial thickness and 25 um thick diffractive LIRIC layer). The LIRIC layer is formed inside of the refractive member 30 as opposed to on either proximal or distal faces.

The particular wavefront pattern(s) formed within the refractive member 30 are created essentially by close-packing solid polymeric elements within the water-based hydrogel to alter the refractive index. One embodiment of the LIRIC wavefront pattern is a phase-wrapped prism wavefront, with a maximum optical phase height of 1 wave at the design wavelength of 555 nm (in the center of the visible spectrum, intended for use by a physician in white light, or alternatively at a phase height of 800 nm intended for use with an infrared camera with an 800 nm illumination wavelength). Other wavefronts may include any of the Zernike polynomials, or combinations thereof, such as prism (i.e., tilt), defocus, spherical aberration, and so on. The wavefronts may be continuous, or discontinuous, as in the case of phase-wrapped aberrations. Examples of phase-wrapped wavefronts would be a Fresnel lens (sphere and/or cylinder), a blazed grating, or phase-wrapped higher order aberrations. Furthermore, the phase-wrapped wavefront may have a peak-to-valley optical path length of an integer number of waves of the design wavelength (e.g., 555 nm in the center of the visible spectrum for viewing by a clinician, or in the near infrared for imaging with a machine vision system) for 100% diffraction efficiency, i.e., a single-vision type of device. Alternatively, the wavefront may be phase-wrapped at a non-integer number of waves of optical path length. This would produce multiple orders of diffraction, leading to a simultaneous, overlayed, view of various retinal regions. The sphere/cylinder, higher order aberrations, and multifocality may also be personalized to an individual to improve the quality of the retinal image.

FIG. 3 is a top plan view of an exemplary refractive button 40 used in the scopes of the present application. The button 40 is shown with a series of linear steps 42 formed therein within an inner layer, as explained. The steps 42 extend across the entire button 40 in one direction, to provide a refractive alteration that enables a physician to look straight through the button 40 and see at a deflection angle within the eye. The deflection angle may vary between about 20-60° depending on the character of the steps 42, as will be explained. Rotation of the button 40 about its axis as described above permits the surgeon to see around the anterior chamber angle, for instance.

FIG. 4 is a top plan view of an alternative refractive button 50 having two different refractive regions 52, 54 in an internal layer therein. A first refractive region 52 has steps that are oriented much like the steps 42 in the button 40 of FIG. 3, and the first region 52 is separated from the second region 54 by an arcuate border 56, roughly separating the two regions into equal sizes. In the second refractive region 54, a series of linear steps 58 are formed which are aligned at an angle to the orientation of the steps in the first refractive region 52. For instance, the steps 58 are at about a 45° angle to the steps in the first refractive region 52. In this way, the physician can look directly through the button 50 and see along two different deflection angles within the eye. As before, rotation of the button 50 about its axis as described above provides even greater flexibility to the surgeon.

FIG. 5 is a top plan view of an alternative refractive button 60 also having two different refractive regions 62, 64 in an internal layer therein. A first refractive region 62 takes up a majority of the surface area within the altered internal layer than a smaller second refractive region 64. In the illustrated embodiment, the refractive regions 62, 64 are separated by a pair of angled radial borders 66, 68, such that the second refractive region 64 forms a pie-shaped segment making up about 30-40% of the total surface area. The first refractive region 62 once again has linear steps that are oriented much like the steps 42 in the button 40 of FIG. 3, while the second refractive region 64 has steps angled at about 45° thereto. This provides a smaller viewing window for the second refractive region 64, which may be useful to the physician in certain circumstances. In the case of a radially asymmetric wavefront pattern, the device may be mounted on a rotational stage to allow the physician to rotate their view.

Finally, FIG. 6 is a top plan view of an alternative refractive button 70 having three different refractive regions 72, 74, 76. Three radial borders 78 that are equidistantly spaced divide the three regions 72, 74, 76 evenly into 120° pie-shaped segments. Linear steps are laser-formed in an internal layer within each region 72, 74, 76 of the button 70. Each of the step angles is oriented 60° from the steps in the next adjacent region to provide the surgeon with multiple refractive viewing angles at once, and along with button axis rotation enables an even greater variety of viewing. Each segment of the optical zone may have a different amount of tilt, a different wavefront aberration (e.g., tilt, defocus).

Alternatives include lenses configured as adjustable, like rotating a multi-objective microscope—i.e., as you rotate the lens relative to the viewer, the viewer sees different angles of the peripheral retina and/or different magnifications. For instance, rotatable scopes with fiducials, or angular marking, which help orient and direct the refractive view may be used. This helps enable different viewing angles and deflection degrees by different regions of the lens so that a technician can rotate through them. Different magnifications for different regions, also delimited by fiducials or other markers, may be incorporated.

Multiple LIRIC devices may be combined. By combining a positive defocus and negative defocus LIRIC device, when separated axially, they shall interact to provide magnification or minification, depending on the relative magnitude of defocus and axial separation. Each LIRIC device may be segmented into several regions (akin to FIG. 6). An amplitude mask may be used as well to limit the physician's field of view through only one intended viewing region.

Figure 8:
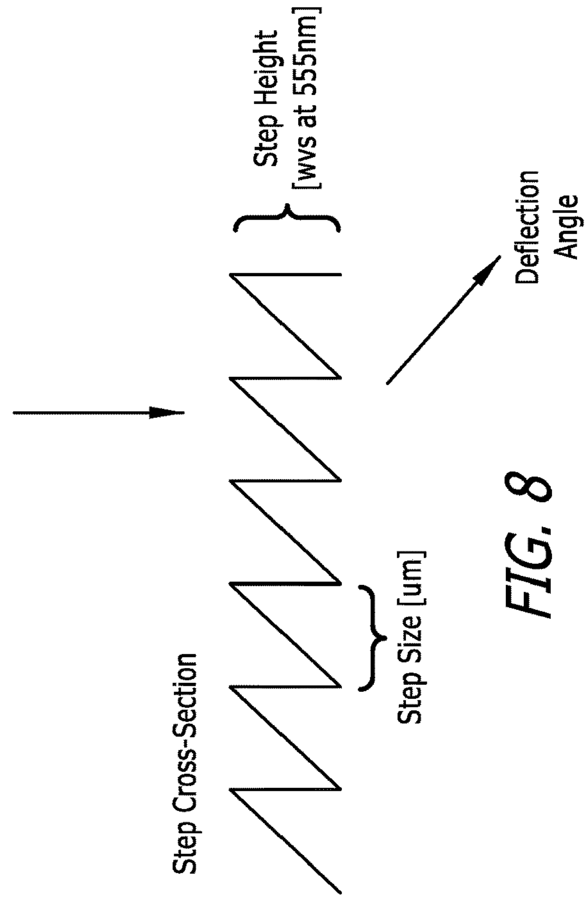
FIG. 8 is a schematic cross-section of one wavefront pattern indicating step size and height.
Figure 7:
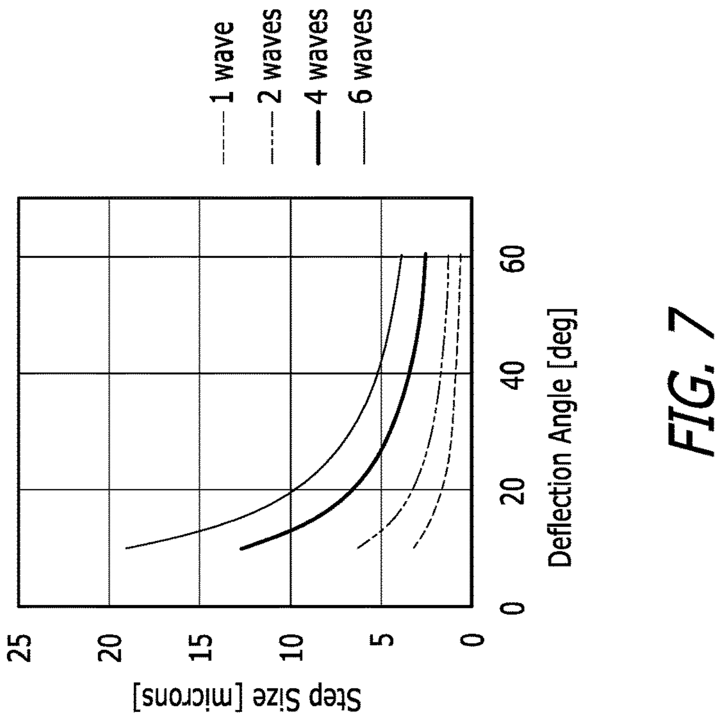
FIG. 7 is a graph showing curves of deflection angle possible for different step sizes for four different wavefront patterns.

FIG. 7 is a graph showing curves of deflection angle possible for different steps sizes for four different wavefront patterns, and FIG. 8 is a schematic cross-section of one wavefront pattern indicating step size and height. It can be seen from FIG. 7, that a smaller maximum LIRIC optical phase height (e.g., 1 wave) requires a smaller step size for a fixed deflection angle. Alternatively, a higher maximum optical phase dictates a larger step size for the same deflection angle. It should be understood that each step schematically shown in section in FIG. 8 is a sawtooth pattern (representing prism), it may also have a profile of a defocus or other useful aberration. Moreover, the particular shape of the steps across any of the refractive buttons may vary for different regions or quadrants. That is, it may be useful to provide smaller steps in one region then another, or a differently shaped step in one region for a particular purpose. The ability to customize the refractive buttons in this manner greatly increases the ability to fine-tune the scope for a variety of needs.

The step size refers to the width of each step, while the step height is the dimension of the step along the Z-axis. FIG. 7 illustrates that as the step size or width decreases for all the wavefront patterns, the resulting deflection angle increases. In general, the smaller the step size the greater the chromatic diffraction (CD). The labels for the 4 curves—which the legend shows as "1 wave," "2 waves," "4 waves," and "6 waves"—refer to the "step height" (in FIG. 8) or the peak LIRIC-induced optical phase value in the LIRIC pattern.

The chromatic diffraction is determined by using a diffraction grating equation at multiple wavelengths, such as the limits of the visible spectrum (e.g., 400 and 700 nm). The diffraction grating equation is shown below:

$$m*\text{lambda}=d*\sin(Q)$$

where m is the order of diffraction, lambda is the wavelength (in micrometers), d is the step size (in micrometers) and Q is the angle of diffraction (in radians). This formula can be rearranged to solve for the diffraction angle:

$$Q=\arcsin(m*\text{lambda}/d)$$

Conversely, increasing the step size reduces chromatic diffraction. However, larger steps sizes require more time and money to machine into the refractive button, and thus there is a threshold beyond which the step size becomes economically impractical. A balance must be found.

Figure 9:
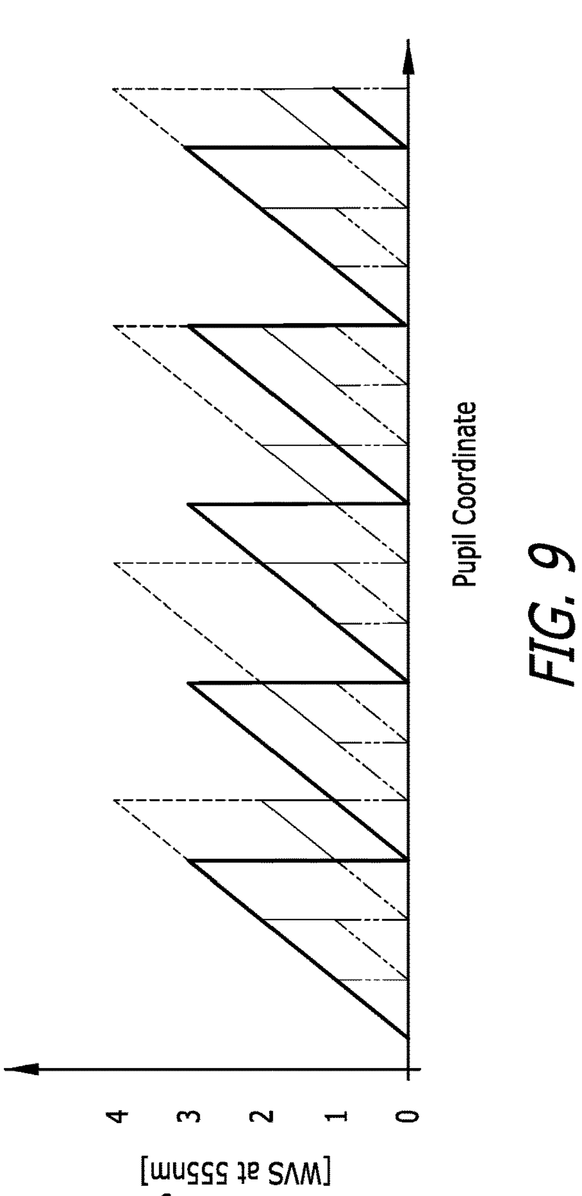
FIG. 9 is a graph of wavefront height of a number of different wavefront patterns superimposed on one another.

FIG. 9 is a graph of wavefront height of a number of different wavefront patterns superimposed on one another, and illustrates the optical phase cross-section of a prismatic LIRIC wavefront for several distinct examples of maximum optical wavefront height. A wavefront phase-wrapped at a height of 1.0 waves represents a pure diffractive wavefront. Alternatively, wavefront with zero phase-wraps represents a pure refractive wavefront. However, wavefronts phase-wrapped at max phase height of 2 or more waves represent a hybrid diffractive-refractive wavefront. The hybrid wavefronts have chromatic aberration between the negative chromatic aberration of a diffractive optic and the positive chromatic aberration of a refractive optic.

Figure 10:
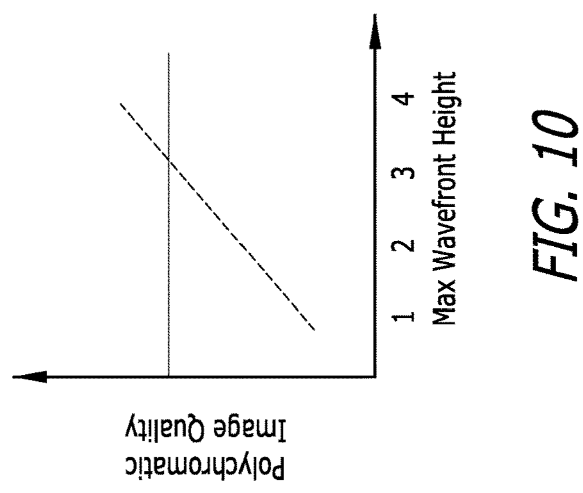
FIG. 10 is a graph of polychromatic image quality for different wavefront heights.

FIG. 10 is a graph of polychromatic image quality for different wavefront heights. As the wavefront height increases, the polychromatic image quality also increases, but again there is a practical maximum beyond which machining becomes too expensive and time-consuming.

Figure 11:
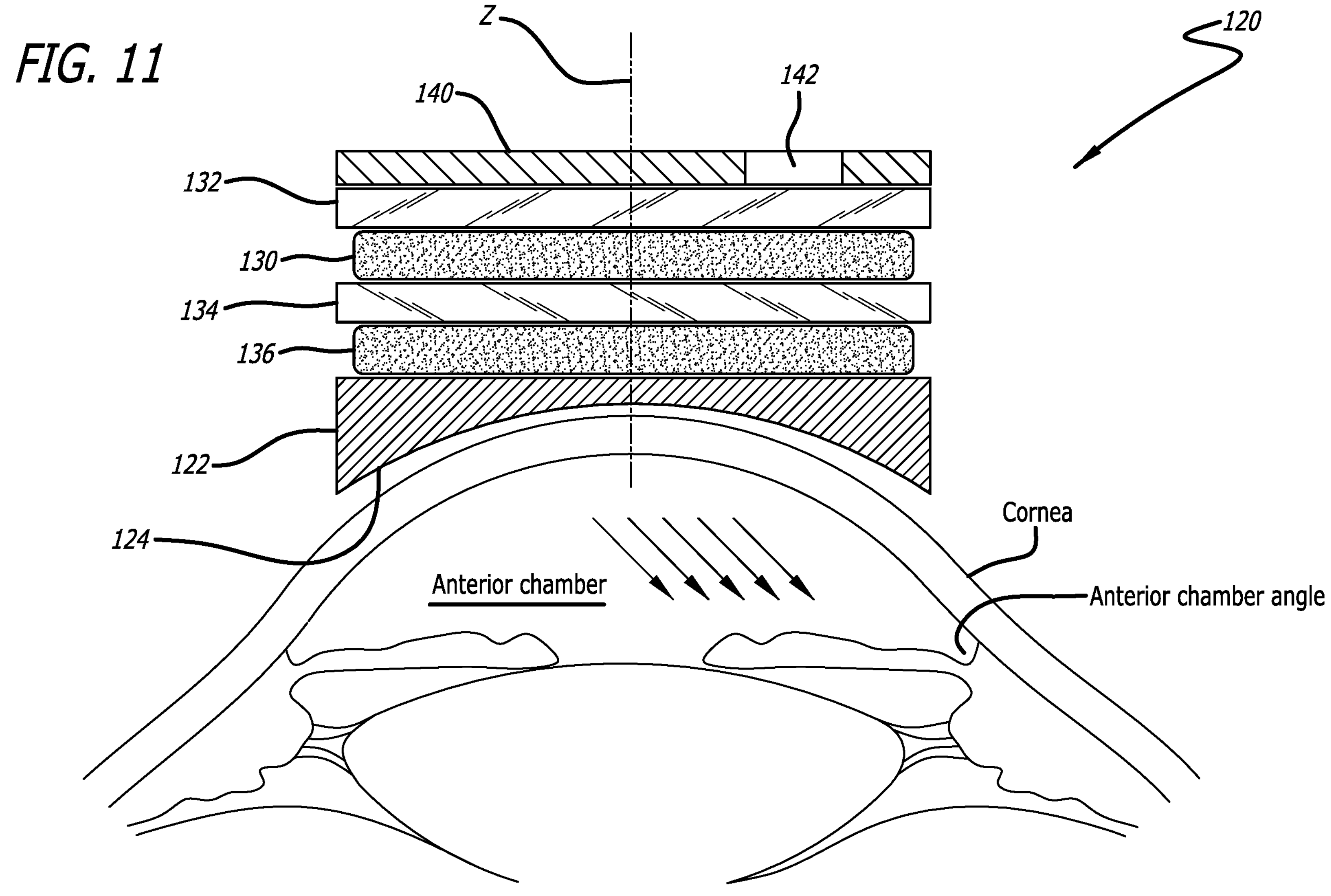
FIG. 11 is a schematic axial sectional view of an alternative scope used for imaging an anterior chamber angle and having cooperating refractive members and a masking element.

FIG. 11 is a schematic axial sectional view of an alternative scope 120 used for imaging an anterior chamber angle. The scope 120 again comprises a patient contact interface or ocular 122 having a curved distal surface 124 for contacting the cornea, often with the use of an index matching lubricating fluid or gel. A first refractive component of the scope 120 is provided by a slim circular refractive member in the form of a disk or button 130 flanked by one slim plate or sandwiched between two slim plates or support members 132, 134. As described above, the "plates" may alternatively be in a three-dimensional structure (i.e., not a slim disk or button), and the term "support members" encompasses a number of such different shapes, including the slim plates 132, 134.

The alternative scope 120 adds a second slim circular refractive member in the form of a disk or button 136, sandwiched between the lower support member 134 and a top surface of the patient contact interface or ocular 122. The two refractive members 132, 136 may be rotatable relative to each other—for example, to alter direction of view and/or magnification. One of the refractive members 132, 136 could include a URIC-modified optical structure to add power for magnification, or alternatively two translatable plates may be used in an Alverez lens configuration to variably change defocus.

Each of the plates 132, 134 as well as the ocular 122 are desirably transparent plastic or glass members with neutral refractive indices so as not to bend or otherwise affect light transmission therethrough. Outer housing members are not shown but are typically included to protect the aforementioned scope 120 components from dirt or damage. Such outer housing members may be made of various plastics, glasses or metals. The housing could also include a suction cup to hold the scope on the eye.

Further, a masking element 140 may be included in the scope 120. The masking element 140 may be configured as a slim disk or bottom, or otherwise, and is opaque except for a window 142 to limit the user's view to one segment through the scope. Desirably, the masking element 140 rotates to enable the user to change the viewpoint, and preferably the masking element 140 rotates relative to one or both of the refractive members 132, 136.

Figure 12A:
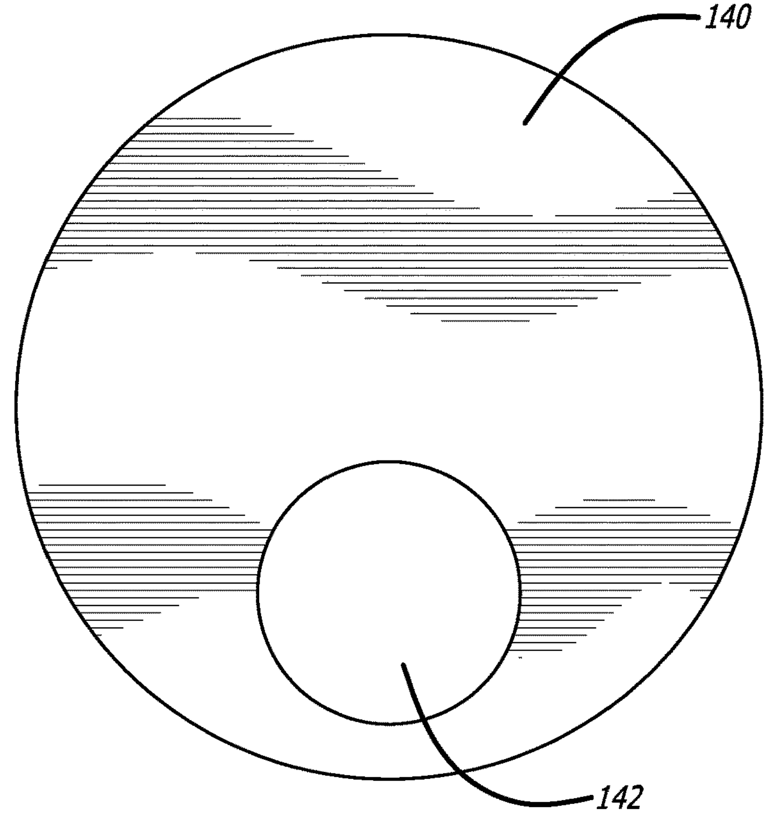
FIGS. 12A and 12B are plan views of different masking elements.
Figure 12B:
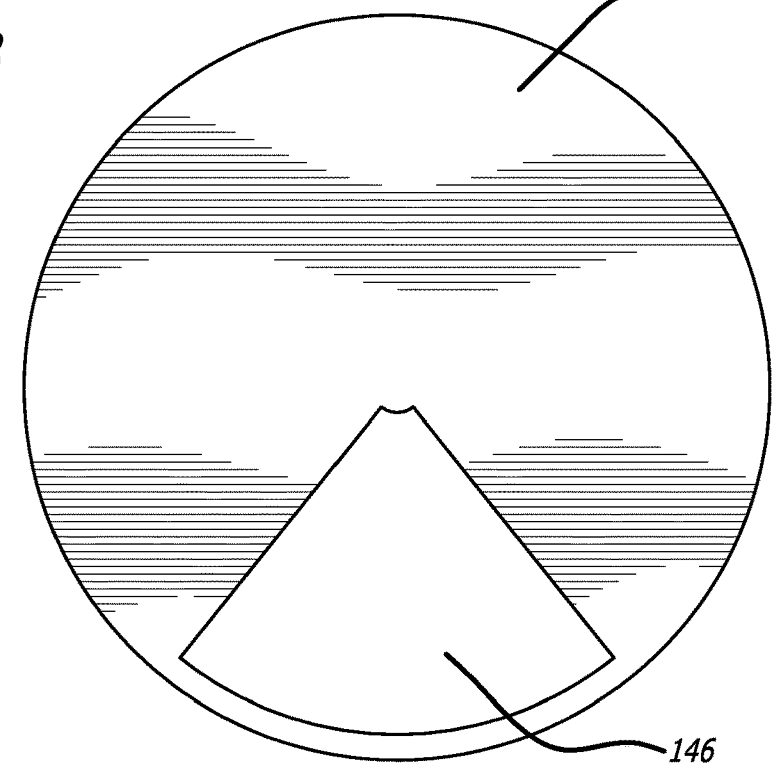

FIGS. 12A and 12B are plan views of different masking elements. A first masking element 140 has a circular open or clear window 142 located off-center from an axis of the masking element and scope 120. Rotation of the masking element 140 thus enables the user to see through the window 142 in different angular regions of the scope 120, which focusses the user on different quadrants through the scope 120. By combining a number of different refractive members 132, 136 (which may also be rotatable), rotation of the masking element 140 relative to the scope 120 illuminates different regions within the eye.

One beneficial outcome of constructing scopes for the eye as disclosed herein is the ability to economically produce scopes made of relatively inexpensive material, rendering them disposable. Currently, gonioscopes on the market are relatively expensive and generally not disposable, requiring the doctor's office to sterilize the expensive equipment. In the present application, the scopes require no minors or microscopes for seeing into the steep angles within the eye, and the cost of each of the scopes makes their one-time use feasible. Moreover, current gonioscopes are relatively bulky and/or heavy, and sometimes require the patient to lie supine rather than upright, while the scopes of the present application will be relatively lightweight and easy to apply to the patient in a sitting position, as in a common eye exam.

The most common application for scopes as described herein is to view the anterior chamber angle for evidence of trabecular meshwork degeneration and/or obstruction. Other applications include using the scope to diagnose disease within various regions of the eye. Peripheral retinal imaging is another possible application, as is imaging haptics on an intraocular lens (IOL) which are normally hidden behind the iris.

The scopes described herein may also be used in conjunction with various treatments. For example, the scopes may be used to guide injections or laser radiation for correcting retinal detachment or operating on blood vessels. The scopes may enable an ophthalmologist to treat peripheral regions of the retina which have previously been outside of the field of view. The scopes may also be used to treat posterior capsule opacification, gene therapy, or for implanting an Argus retinal prosthetic. Another use is in aid of installation of glaucoma shunts.

While the invention has been described in its preferred embodiments, it is to be understood that the words which have been used are words of description and not of limitation. Therefore, changes may be made within the appended claims without departing from the true scope of the invention.

What is claimed is:

1. An eye scope, comprising:

a polymer member having a refractive index and a proximal and distal side, with the distal side towards an eye, wherein the polymer member has a central axis perpendicular to both the proximal and distal sides;

the polymer member having an internal layer with a refractive index having a wavefront pattern that deflects light passing through the polymer member from the distal to the proximal side;

a transparent rigid support member is positioned on a side of the polymer member; and a transparent patient contact interface positioned distal to the rigid support member, which is positioned distal to the polymer member, wherein the eye scope may be placed with the patient contact interface in contact with a patient's cornea; and a second polymer member having an internal layer modified by femtosecond laser micromachining to have a wavefront pattern that deflects light passing through the second polymer member from the distal to the proximal side, the second polymer member being positioned on the distal side of the rigid support member, wherein an observer may look through the eye scope to view interior details of an eye that are at an angle from the central axis of the eye.

2. The eye scope of claim 1, wherein one or both of the first and second polymer members is/are rotatable relative to the patient contact interface.

3. The eye scope of claim 1, wherein the polymer member is flat on both sides.

4. The eye scope of claim 1, wherein the polymer member is a hydrogel polymer.

5. The eye scope of claim 1, wherein the polymer member is rotatable relative to the patient contact interface.

6. The eye scope of claim 1, wherein the transparent rigid support member is on the distal side of the polymer member, and further including a transparent second rigid support member positioned on the proximal side of the polymer member.

7. The eye scope of claim 6, further including a masking element positioned on the proximal side of the second rigid support member.

8. The eye scope of claim 7, wherein the masking element is rotatable relative to the second rigid support member.

9. The eye scope of claim 7, wherein the masking element is opaque except for an open or clear window in one segment thereof.

10. The eye scope of claim 1, wherein the eye scope is configured to image an anterior chamber angle of the eye through the light deflected through the polymer member.

11. The eye scope of claim 1, wherein the eye scope is configured to image annular regions of the retina at 0-15 degrees and 15-30 degrees through the light deflected through the polymer member.

12. An eye scope, comprising:

a polymer member having a refractive index and a proximal and distal side, with the distal side towards an eye, wherein the polymer member has a central axis perpendicular to both the proximal and distal sides;

the polymer member having an internal layer modified by femtosecond laser micromachining to alter the with a refractive index having a wavefront pattern that deflects light passing through the polymer member from the distal to the proximal side, wherein the polymer member internal layer has two or more regions, wherein each region has a different optical effect due to the refractive index in each region; and a transparent first rigid support member is positioned on a distal side of the polymer member and a transparent second rigid support member is positioned on the proximal side of the polymer member, the first and second rigid support members and the polymer member being affixed together in a subassembly;

a transparent patient contact interface is positioned distal to the subassembly, wherein the eye scope may be placed with the patient contact interface in contact with a patient's cornea, wherein the subassembly is rotatable relative to the patient contact interface, and wherein an observer may look through the eye scope to view interior details of an eye that are at an angle from the central axis of the eye.

13. The eye scope of claim 12, further including a second polymer member having an internal layer modified by femtosecond laser micromachining to have a wavefront pattern that deflects light passing through the second polymer member from the distal to the proximal side, the second polymer member being positioned between the first rigid support member and the patient contact interface.

14. The eye scope of claim 12, wherein the polymer member is flat on both sides.

15. The eye scope of claim 12, wherein the polymer member is a hydrogel polymer.

16. The eye scope of claim 12, further including a masking element positioned on the proximal side of the second rigid support member.

17. The eye scope of claim 16, wherein the masking element is rotatable relative to the second rigid support member.

18. The eye scope of claim 16, wherein the masking element is opaque except for an open or clear window in one segment thereof.

19. The eye scope of claim 12, wherein the different optical effect on the light passing through the polymer member in each region is at least one of the following: deflection angle; optical power or magnification; defocus; cylinder; wavefront aberrations; multifocality; chromatic aberrations; and masking elements.

20. An eye scope, comprising:

a polymer member having a refractive index and a proximal and distal side, with the distal side towards an eye, wherein the polymer member has a central axis perpendicular to both the proximal and distal sides;

the polymer member having an internal layer with a refractive index having a wavefront pattern that deflects light passing through the polymer member from the distal to the proximal side; and a transparent rigid support member is positioned on a side of the polymer member, wherein the polymer member internal layer has two or more regions, wherein each region has a different optical effect due to the refractive index in each region, wherein an observer may look through the eye scope to view interior details of an eye that are at an angle from the central axis of the eye.

21. The eye scope of claim 20, wherein the different optical effect on the light passing through the polymer member in each region is at least one of the following: deflection angle; optical power or magnification; defocus; cylinder; wavefront aberrations; multifocality; chromatic aberrations; and masking elements.

22. The eye scope of claim 20, wherein the polymer member is flat on both sides.

23. The eye scope of claim 20, wherein the polymer member is a hydrogel polymer.

24. The eye scope of claim 20, wherein the polymer member is rotatable relative to the patient contact interface.

25. The eye scope of claim 20, wherein the transparent rigid support member is on the distal side of the polymer member, and further including a transparent second rigid support member positioned on the proximal side of the polymer member.

26. The eye scope of claim 25, further including a masking element positioned on the proximal side of the second rigid support member.

27. The eye scope of claim 26, wherein the masking element is rotatable relative to the second rigid support member.

28. The eye scope of claim 26, wherein the masking element is opaque except for an open or clear window in one segment thereof.

29. The eye scope of claim 20, wherein the eye scope is configured to image an anterior chamber angle of the eye through the light deflected through the polymer member.

30. The eye scope of claim 20, wherein the eye scope is configured to image annular regions of the retina at 0-15 degrees and 15-30 degrees through the light deflected through the polymer member.

* * * * *